United States Patent [19]

Jannard

[11] Patent Number: 4,867,550
[45] Date of Patent: * Sep. 19, 1989

[54] TOROIDAL LENS FOR SUNGLASSES

[75] Inventor: James H. Jannard, Laguna Niguel, Calif.

[73] Assignee: Oakley, Inc., Irvine, Calif.

[*] Notice: The portion of the term of this patent subsequent to Jun. 23, 2004 has been disclaimed.

[21] Appl. No.: 151,173

[22] Filed: Feb. 1, 1988

Related U.S. Application Data

[63] Continuation-in-part of Ser. No. 893,091, Aug. 4, 1986, abandoned, which is a continuation-in-part of Ser. No. 787,242, Oct. 15, 1985, Pat. No. 4,730,915, which is a continuation-in-part of Ser. No. 690,642, Jan. 11, 1985, Pat. No. 4,674,851.

[51] Int. Cl.$^4$ .............................................. G02C 9/00
[52] U.S. Cl. ........................................ 351/47; 351/44
[58] Field of Search ................. 351/44, 47, 62, 103, 351/109, 158, 159; 2/426, 429

[56] References Cited

U.S. PATENT DOCUMENTS

| | | |
|---|---|---|
| 145,288 | 7/1846 | Di Cicco . |
| 163,869 | 7/1851 | Hinman . |
| 176,316 | 12/1855 | Fleming . |
| 178,178 | 7/1856 | Fleming . |
| 187,394 | 3/1860 | Moeller . |
| 199,150 | 9/1864 | Carmichael . |
| 210,048 | 1/1868 | Imperatrice . |
| 268,683 | 4/1883 | Tenny . |
| 285,020 | 9/1886 | Schmidthaler . |
| 2,444,498 | 7/1948 | Cochran . |
| 2,472,731 | 6/1949 | Splaine . |
| 2,482,664 | 9/1949 | Gagnon . |
| 2,582,345 | 1/1952 | Moeller . |
| 3,133,982 | 5/1964 | Janz . |
| 3,233,249 | 2/1966 | Baratelli et al. . |
| 3,233,250 | 2/1966 | Jonassen . |
| 3,531,189 | 9/1970 | Petito . |
| 3,689,136 | 9/1972 | Atamian . |
| 3,708,224 | 1/1973 | Linblom . |
| 3,756,704 | 9/1973 | Marks . |
| 4,515,448 | 5/1985 | Tackles .............................. 351/41 |
| 4,564,272 | 1/1986 | Kan . |

FOREIGN PATENT DOCUMENTS

| | | |
|---|---|---|
| 673815 | 1/1930 | France . |
| 790755 | 11/1935 | France . |
| 2472764 | 7/1981 | France . |

OTHER PUBLICATIONS

Picture of Oakley Blades as First Worn 8/27/85.

*Primary Examiner*—Rodney B. Bovernick
*Assistant Examiner*—R. M. Dzierzynski
*Attorney, Agent, or Firm*—Knobbe, Marten, Olson & Bear

[57] ABSTRACT

Disclosed is a toroidal lens for use in a pair of sunglasses, comprising a unitary pane of transparent material which is curved about each of two substantially perpendicular axes, each having a substantially constant radius such that the lens defines a portion of the surface of a toroid. A cross-section taken along the horizontal axis of the lens reveals an arcuate configuration which may be characterized as having a rfadius $R_1$. A cross-section taken along a vertical axis reveals an arcuate configuration through the lens having a radius designated $R_2$. Optimally, $R_2 \geq 1.10 R_1$, and the length of the lens along the horizontal arcuate cross-section is in the range of from about 5½ inches to about 7 inches. The lens may have either a uniform thickness throughout, or may taper from a greater thickness in a region centered about the midpoint, generally above the nose of a wearer, to a lesser thickness near the peripheral ends of the lens.

13 Claims, 4 Drawing Sheets

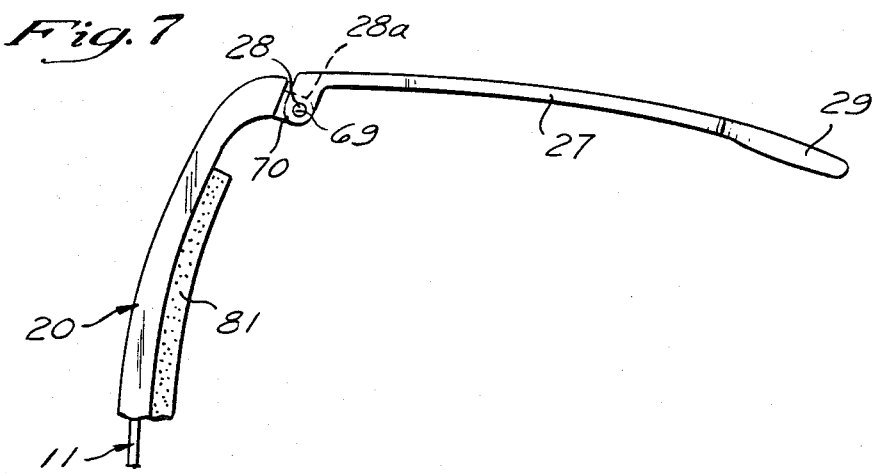
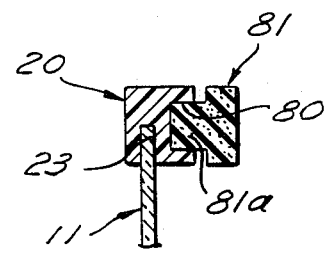
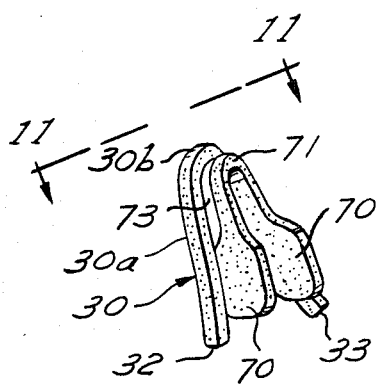
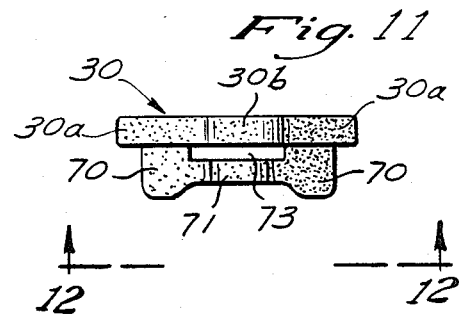

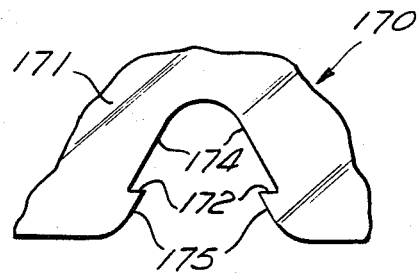
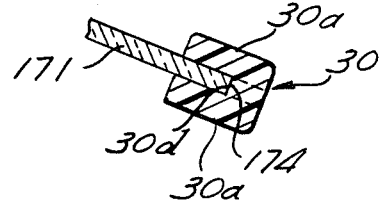
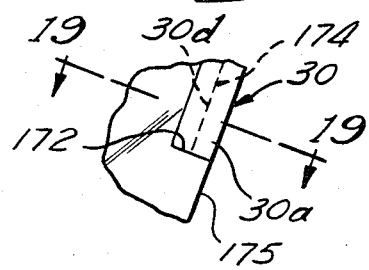
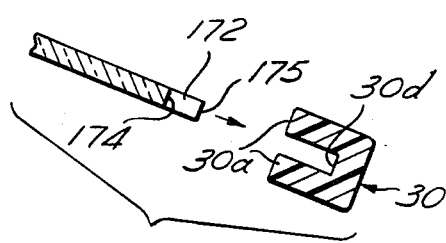
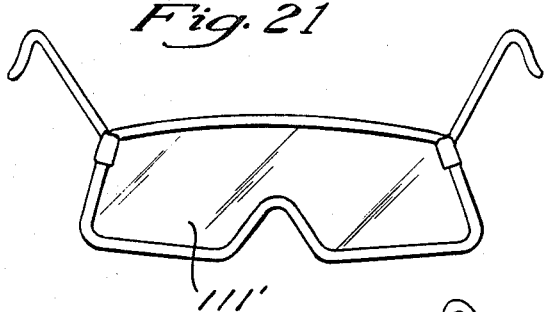
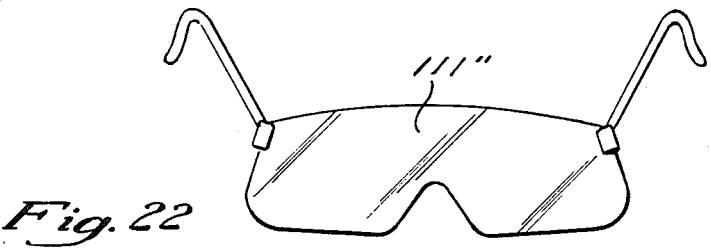

TOROIDAL LENS FOR SUNGLASSES

BACKGROUND OF THE INVENTION

This application is a continuation-in-part of Ser. No. 893,091, now abandoned filed Aug. 4, 1986, which is a continuation-in-part of Ser. No. 787,242, filed Oct. 15,1985 now U.S. Pat. No. 4,730,915, which is a continuation-in-part of Ser. No. 690,642, filed Jan. 11, 1985, issued June 23, 1987, as U.S. Pat. No. 4,674,851.

The present invention relates to a lens for sunglasses and, more particularly, to a unitary, high quality lens having exceptional optical clarity, and which extends substantially unobstructed throughout the wearer's entire angular range of vision. The lens of the present invention maximizes the interception of peripheral light and, due to the unique toroidal configuration of the lens, maximizes the distance from the eye to the lens while at the same time retaining good aerodynamic properties.

In addition to permitting sufficient ventilation to remain comfortable and resist fogging, the lens of the present invention also permits construction of sunglasses which conform closely to the front and sides of the wearer's head. The resulting low profile glasses utilizing the lens of the present invention are particularly suited for such situations as competition skiing or bicycle racing which require precise optical resolution and aerodynamic efficiency. The toroidal lens of the present invention may also be advantageously used in eyewear design for underwater use, which also requires close conformation of the lens to the front and sides of the wearer's head, and also adequate clearance between the eye and the lens.

The lineage of current generation specialty eyewear began with the dual lens system, wherein a separate lens was provided for each eye generally cut from a spherical or planar blank. Efforts to eliminate peripheral light and make other improvements to the spherical or planar dual lens systems are described in my co-pending application Ser. No. 65,345, which is incorporated by reference herein.

The unitary, molded, frusto-conical lens blank was then developed, such as that disclosed in U.S. Pat. No. 4,515,448 to Tackles. Although diffraction gradients were minimized by molding the lens with a predetermined curvature, the unitary frusto-conical lens remains unsatisfactory for several reasons.

The next improvement in specialty eyewear utilized a unitary lens curved about an axis having a substantially constant radius throughout, such that the lens defined a portion of the wall of a cylinder. This lens is the subject of my co-pending application Ser. No. 65,345.

Notwithstanding the advantages of the cylindrical lens system for certain applications, there remains a need for a specialty lens having both excellent optical and aerodynamic properties and interception of peripheral light, yet at the same time having a low profile, adequate ventilation and sufficient room between the eye and the lens to maximize comfort.

SUMMARY OF THE INVENTION

There has been provided, in accordance with one aspect of the present invention, a unitary curved lens for mounting in a frame to form a pair of eyeglasses, conformed to extend in the path of the wearer's left and right eye fields of vision. The unitary lens of the present invention is curved along each of two substantially perpendicular axes to produce a lens of generally toroidal configuration. Thus, a cross-section of the lens taken along a horizontal plane midway from the bottom of the lens to the top of the lens will reveal an arcuate cross-sectional configuration characterized by a first radius dimension $R_1$. Similarly, a vertical cross-section through the lens will reveal an arcuate configuration characterized by a second radius dimension $R_2$. Preferably, $R_1$ is in the range of from about 2 inches to about 4 inches, and $R_2 \geq 1.10 R_1$.

The lens is adapted to be removably secured to an eyeglass frame, which comprises a left and right ear stem for supporting the frame on the wearer's head. The lens may alternatively be mounted directly to the ear stems alone. In addition, the lens is provided with an upwardly humped lower edge to permit the lens to be further supported upon the wearer's nose.

In a further embodiment of the lens of the present invention, the unitary lens comprises a central region which is substantially symmetrically located with respect to the nose opening, and a pair of distal regions adjacent either side of the central region, wherein the thickness of the lens is greater in the central region than it is at any point within at least one of the distal regions. Optimally, the thickness of the lens at a point approximately 45° along the horizontal arc characterized by $R_1$ from the midpoint of the lens is from about 40% to about 99% of the thickness of the lens at the midpoint.

Further objects, features and advantages of the present invention will become apparent from the detailed description of preferred embodiments which follows, when considered together with the attached figures and claims.

BRIEF DESCRIPTION OF THE DRAWINGS

FIG. 7 is a partial top plan view showing the frame, padding and stem hinge structure;

FIG. 8 is an enlarged fragmentary section showing tang interfit of the unitary pane and top frame;

FIG. 9 is an enlarged section taken on lines 9—9 of FIG. 2 to show frame slots for both the pane and padding;

FIG. 10 is a perspective view of a nose piece with attached elastomeric pads to engage the sides of the wearer's nose;

FIG. 11 is a top plan view on lines 11—11 of FIG. 10;

FIG. 12 is a front view on lines 12—12 of FIG. 11;

FIG. 17 is a schematic view, like FIG. 16, but showing fit of the lens to a wearer's face at an eye location, and having $R_2$ shortened for the purpose of illustration;

FIG. 18 is a fragmentary front view of a modified lens sheet;

FIG. 19 is an enlarged frontal view showing fit of a nose piece to the FIG. 18 lens sheet;

FIG. 20 is an enlarged section taken on lines 20—20 of FIG. 19;

FIG. 21 is a view, like FIG. 20, but showing inward retraction of a grooved nose piece from the lens sheet edge for removal of the nose piece;

FIG. 22 is a frontal view of a lens sheet, as in FIGS. 15 and 16, but with a full frame fitted to the lens sheet; and FIG. 23 is a frontal view of a lens sheet, as in FIGS. 15 and 16, but with ear stems directly connected to the lens sheet.

DETAILED DESCRIPTION OF PREFERRED EMBODIMENTS

Figure 1:
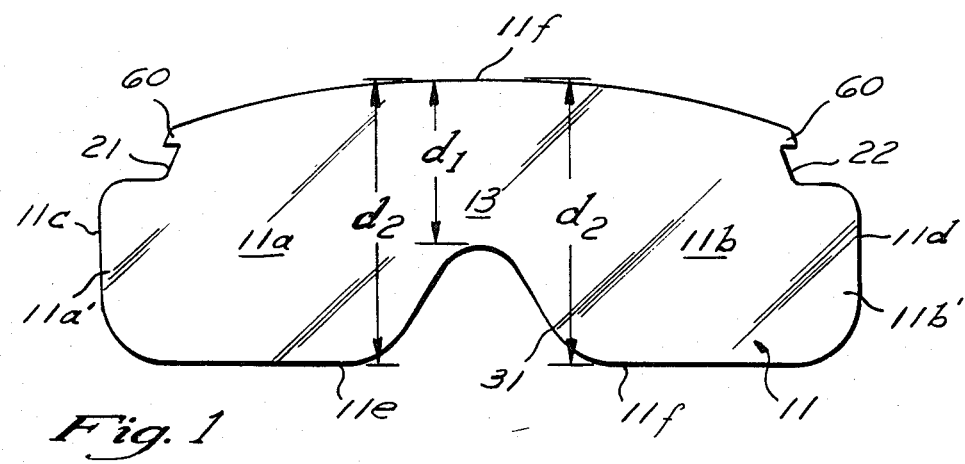
FIG. 1 is a front elevational view of a unitary pane of the present invention in flattened condition.
Figure 2:
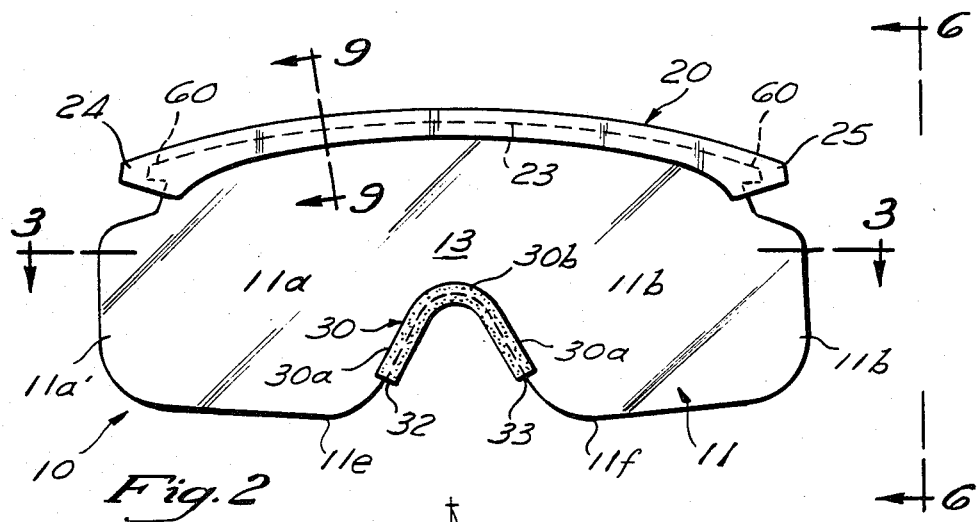
FIG. 2 is a front elevational view of sunglasses incorporating the invention.

Referring to FIGS. 1 and 2, there has been provided in accordance with one aspect of the present invention a unitary curved lens 11 for mounting in a frame 20 to form a pair of eyeglasses 10, conformed to extend in the path of the wearer's left and right eye fields of vision.

The unitary lens 11 of the present invention is curved along each of two substantially perpendicular axes to produce a lens of generally toroidal configuration. The toroidal configuration accrues the styling and aerodynamic advantages described above, as well as providing sufficient clearance within the lens so that the wearer's eyelashes do not come in contact with the interior surface thereof. Such contact can be a significant disadvantage during demanding activities like skiing or bicycle racing, or with the use of low profile underwater goggles which are difficult to clear when in use.

Figure 3:
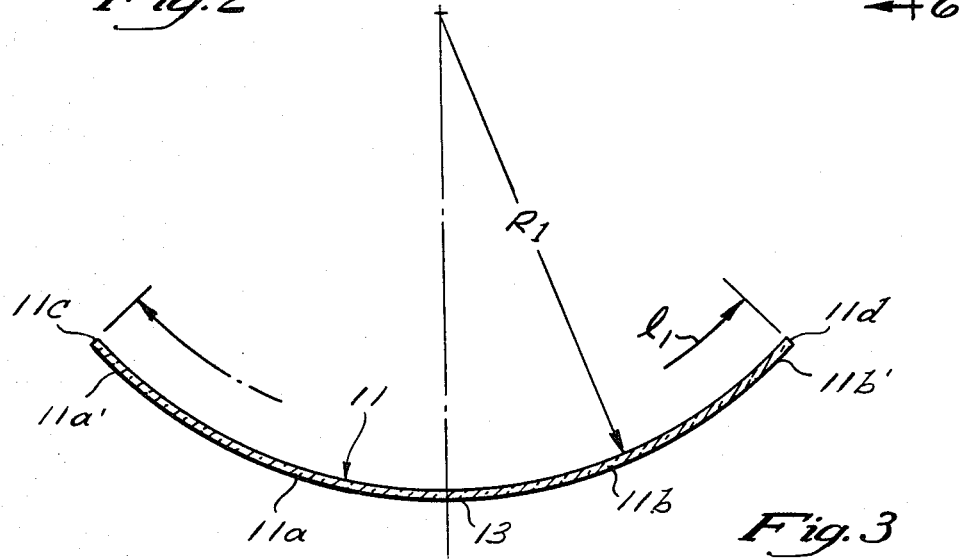
FIG. 3 is a section on lines 3—3 of FIG. 2 normal to the vertical axis of the lens, showing a first embodiment thereof.

As shown in FIG. 3, the curvature of the present lens 11 permits it to conform closely from side-to-side to the wearer's face, thus maximizing the interception of sun and light from other strong sources, while at the same time providing comfort, aerodynamic stability and pleasing aesthetic characteristics. The unitary aspect of the lens of the present invention eliminates the need for multiple frame support mechanisms and enhances the unobstructed field of the wearer's vision.

Figure 15:
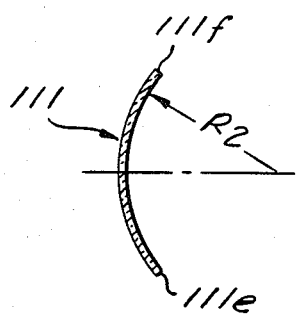
FIG. 15 is a top plan view of the lens of the present invention with the $R_2$ radius less than $R_1$ for the purpose of illustration.

The lens of the present invention may be conveniently described by reference to a front elevational view, such as in FIG. 1, in which an arc along the horizontal length L of the lens, i.e., from a first ear stem to a second ear stem is defined by a radius designated $R_1$ in FIGS. 3 and 15. An arc along the vertical extent of the lens is characterized by the radius $R_2$. See FIG. 16, which illustrates the lens as having a greater curvature, i.e., shorter $R_2$ radius than actual, for the purpose of illustration. The relationship of the radii $R_1$ to $R_2$ is important to accruing the advantages of the present invention, and will be detailed, infra.

Optimally, the lens 11 has a radius of curvature $R_1$ in the "as-molded" condition which is substantially unchanged by mounting the lens 11 in a pair of eyeglass frames 20. It has been determined that optical properties of a lens are detrimentally affected by deviations from the as-molded condition. For example, bending a lens cut from flat sheet stock or a flat molded blank to provide a curved pane inherently results in minor variations in the radius along the arc length of the lens. Variations in the light diffraction properties of the lens result, which introduce distortion. In addition, bending a lens can also result in stress fractures or other compression or expansion induced flaws which can impair the optical qualities of the lens.

Thus, the lens is preferably pre-molded to the desired configuration. Although a variety of radii might accrue the advantages of the present invention, the lens is preferably molded to a radius $R_1$ which is within the range of from about 2.00 to about 4.00 inches, and preferably within the range of from about 2.75 to 3.50 inches.

The radius $R_2$ will always be greater than the radius $R_1$. Preferably, $R_2$ will exceed $R_1$ by at least 10% and, more preferably, $R_2$ will exceed $R_1$ by at least about 15%. For example, $R_2$ is generally within the range of from about 110% to about 400% $R_1$ and, preferably, $R_2$ is within about 150%–300% $R_1$.

Figure 4:
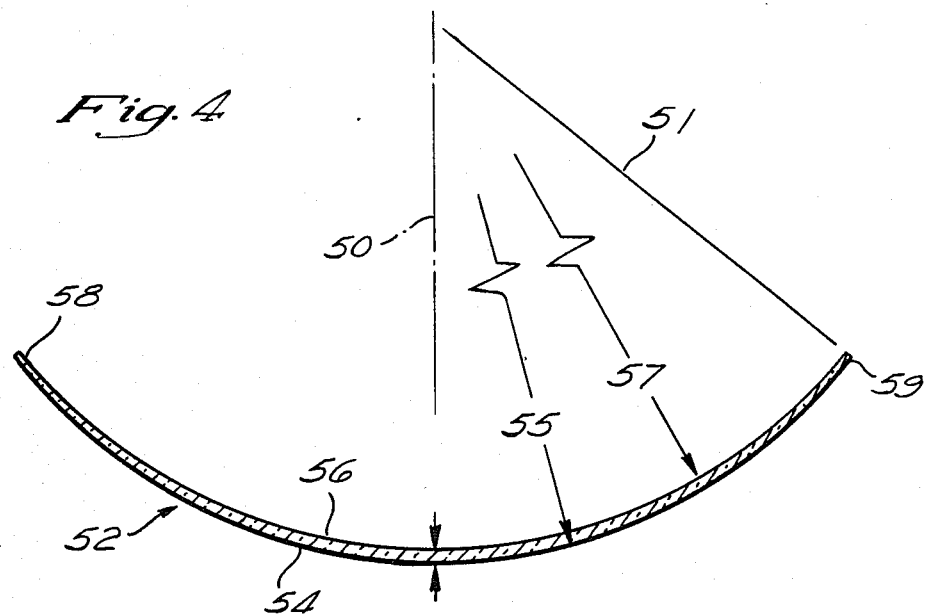
FIG. 4 is a sectional view like FIG. 3, of a different embodiment of the lens of the present invention.
Figure 5:
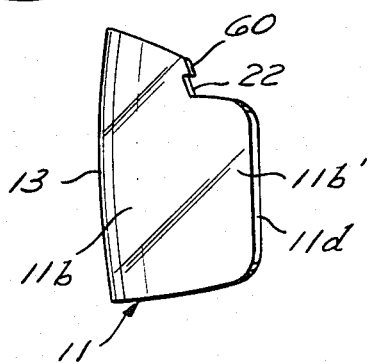
FIG. 5 is a side view of the lens of the present invention in as-molded condition.

The foregoing radius dimensions represent the distance from an axis to the arc which defines the interior, concave surface of the lens, such as radius 57 in FIG. 4. The lens of the present invention has sufficient thickness that it is not accurately defined as having only a single radius. Instead, the lens has a thickness or depth dimension along its entire arc length which causes the arc defined by the outer convex surface 54 to have a different radius 55 than the radius 57 of the arc defined by the inner concave surface 56 of the lens. Hence, in an embodiment where the lens is of substantially uniform thickness throughout, and the axes are coincident, the radius of the outer convex surface is essentially equal to the sum of the radius of the inner concave surface and the depth or thickness of the lens in the foregoing embodiment.

In accordance with another aspect of the present invention, there has been provided a unitary lens substantially as described above, with the following modification. Referring to the horizontal sectional view of the present embodiment, as illustrated in FIG. 4, there is disclosed a lens 52 defined between an outer convex surface 54, having a radius 55 and an inner concave surface 56, having a radius 57. The principal difference from the previously detailed embodiment is that the thickness of the lens 52 at each of the distal ends 58 and 59 is less than the average thickness of the lens at every point intermediate the two distal ends 58 and 59. In addition, the thickness of lens 52 measured at at least one point intermediate the two ends 58 and 59 is greater than the thickness at each of those ends.

The invention can best be understood by reference to FIG. 4, which illustrates the relationship between the lens thickness and the angular position along the horizontal arc length of a lens. Since the arc length L of a lens can be varied considerably, although it is preferably within the range of from about 5.50 to 7 inches, reference points will arbitrarily be selected at the center line 50 and at the 45° line 51. Thus, since the distance from center line 50 to reference line 51 is ⅛ of 360°, the reference arc length for a radius of 3 inches is about 4.7 inches, which is below the preferred minimum arc length, and thus will define a point on the lens.

In accordance with the tapered lens embodiment of the present invention, the thickness of the lens at reference line 51 is preferably from about 40% to about 99% of the thickness at center line 50. Thus, for example, a lens having a center line thickness of about 0.060 inch will preferably have a thickness of within the range of about 0.024 to about 0.059 inch at reference line 51, and a thickness near the distal end within the range of about 0.020 to about 0.055 inch. The thickness of the lens at the midpoint is preferably within the range of from about 0.050 to about 0.090 inch.

Preferably, the thickness of the lens tapers at a substantially even rate from the widest region which is centered about center line 50 to narrower regions near each of the distal ends 58 and 59. In this manner, optical distortion is minimized, as has previously been discussed. By even rate of taper, it is meant that the taper results from the convergence of an arc defining the outer surface 54 of lens 52 and an arc defining the inner surface 56 of lens 52, each arc characterized by substantially constant radii 55 and 57, respectively. Conformation of the lens surfaces to substantially constant radius curves accrues important optical advantages.

The foregoing may be accomplished in a variety of ways, such as, for example, by making radius 55 equal to radius 57 and displacing the center points from each other. Alternatively, radius 55 may be greater or lesser than radius 57, so long as the converging geometry results.

In the production lens, of course, the distal ends 58 and 59 are formed well before the continuation of the arcs defining surfaces 54 and 56 converge. In a toroidal lens produced in accordance with this embodiment, for example, and having a center line thickness of approximately 0.060 inch, the thickness at either distal end 58 and 59 will generally be within the range of from about 0.040 to about 0.055 inch.

Finally, since a portion of the lens 52 near the distal ends 58 and 59 serves primarily to block peripheral light and is likely outside of the wearer's line of vision, it is less crucial that the radius of curvature be constant in this area. Thus, the lens may be provided with an even rate of taper only up to a certain point intermediate the reference line 51 in FIG. 4 and the distal end 59. From near that point until the distal end 59, the lens 52 may be provided with a relatively constant thickness or a taper of a different rate. Perhaps less desirable from a manufacturing standpoint, this embodiment could still accrue the advantages of the present invention.

The preceding discussion pertains to the contour of the lens, as distinguished from its shape, which will now be discussed. The shape of one embodiment of the lens may be best understood by reference to FIGS. 1 and 2, although many other shapes can be envisioned which will accrue the advantages of the present invention.

A first eye pane 11a and a second eye pane 11b are located directly in front of the wearer's right and left eyes, respectively, and are merged together with a unitary bridge portion 13. In addition, the distal portion 11a' of eye pane 11a, for example, continues along the arc path of the lens 11, as discussed above in connection with FIG. 3, such that it preferably traverses the entire angular range of vision for the corresponding eye. Similarly, the distal portion 11b' of eye pane 11b extends substantially all the way across the wearer's angular range of vision for the other eye. In this manner, a substantial amount of light which approaches the eye from a peripheral direction will travel through the lens before reaching the wearer's eyes.

The objective of shielding against peripheral light is best accomplished in a lens having a radius within the above-stated ranges, if the arc length of the lens is within the range of from about 5.50 to about 7 inches. The arc length of the lens is the length along the surface of the lens from a first distal end 11c to a second distal end 11d, as illustrated in FIGS. 1 and 3.

Figure 16:
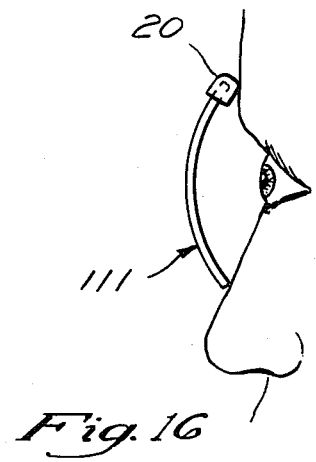
FIG. 16 is a section taken on lines 16—16 of FIG. 15 with $R_2$ shortened for the purpose of illustration.

Another aspect of the lens of the present invention is that not only does it effectively block peripheral light, but it still permits sufficient ventilation to remain comfortable and to resist fogging. Referring to FIG. 16, it can be seen that the uppermost edge 111f and lowermost edge 111e will lie on the surface of a cylinder. Thus, the toroid lens can accrue the advantages associated with substantially cylindrical unitary lenses. A top frame 20 can be provided for supporting the lens 11 which closely conforms to the shape of the wearer's forehead. This provides a seal against wind which, for example, in the case of the bicycle rider, is directed at a downward angle between the lens and the wearer's forehead. In addition, a band of an absorbent material 80 can be disposed between the frame 20 and the forehead to prevent perspiration from entering the wearer's eyes. See, for example, FIGS. 7 and 9. Alternatively, a frame may be provided which only borders the sides and/or bottom edge of the lens, (not illustrated), or which completely surrounds the lens. See FIG. 22. Finally, the ear stems may be secured directly to the lens, as in FIG. 23, without any frame at all.

At the same time, an imaginary secant drawn between edges 111f and 111e (FIG. 16), parallel to the vertical axis of the lens, gradually increases in distance from top to bottom away from the receding profile of the wearer's face, which is roughly defined by a frusto-conical curve. Thus, a ventilation gap results between the lower edges 11e and 11f of eye panes 11a and 11b, respectively (FIG. 1), and the wearer's face. This is a significant advantage over prior art frusto-conical lenses. For a lens dimensioned as described herein, the ventilation gap will be roughly from about 3/16 to about 5/16 inch greater than the corresponding gap, if any, in the frusto-conical system. The lens of the present invention additionally is advantageous over the cylindrical lens system since, in addition to accruing the ventilation advantages thereof, the lens of the present invention provides sufficient space between the eye and the lens to avoid eyelash contact.

The size of the ventilation gap will also depend in part upon the height $d_2$ of the lens, illustrated on eye pane 11b of FIG. 1 for convenience. It is understood that the height of the eye panes 11a and 11b will be essentially the same, and the discussion in connection with one is intended to apply to both. The height $d_2$ of the lens 11 of the present invention, measured from the top 11f of the lens 11 to the bottom edge 11e may be varied to optimize various functional and aesthetic considerations, but will typically fall within the range of from about 1.75 to about 3 inches, and preferably between about 2 and 2.75 inches. As previously discussed the two eye panes 11a and 11b merge into a unitary lens by way of a connecting bridge portion 13. The distance $d_1$ from the top 11f of the lens to the lower edge of the bridge portion 13 may also vary, but preferably is within the range of from about 0.75 to about 1.50 inches.

Referring to FIG. 2, the lens of the present invention may be provided with a top frame 20 extending along and bounding the upper edge of the lens or pane 11, which may be either the substantially constant thickness lens illustrated in FIG. 3 or the tapered thickness lens illustrated in FIG. 4. Frame 20 preferably bounds the upper edge of lens 11 along the area between the notched areas 21 and 22 formed immediately above the individual eye panes 11a and 11b. The frame advantageously consists of relatively rigid molded plastic material, which may be transparent or dyed any of a variety of colors.

Figure 13:
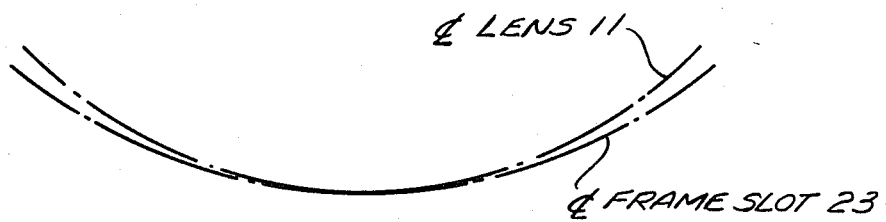
FIG. 13 is a diagram to show mismatch between interfits of the pane and top frame.
Figure 14:
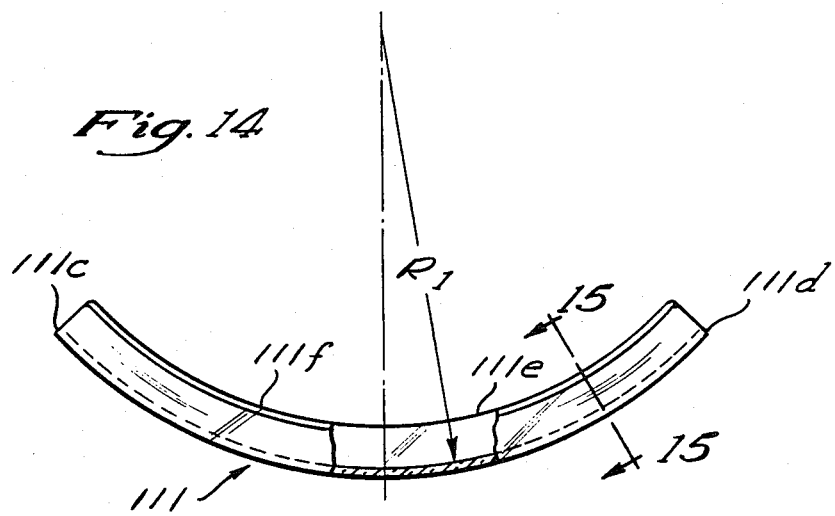

The top frame 20 is shown as being removably attached to the top edge of the lens 11. For this purpose, a slot 23 is formed upwardly therein from the bottom of the frame 20, with the curvature generally matching that of the lens to tightly, yet removably receive the lens upper edge. The curvature of the slot 23 may be slightly different than the as-molded $R_1$ curvature of the lens, to provide a mismatch, to grip the pane, which then resiliently co-acts with the frame to very slightly deform the pane and enhance a friction engagement. See FIG. 13. Note that the lens upper edge is shown to have slight upward convexity, as illustrated in FIGS. 1 and 2.

Fastening means such as one or more tangs 60 integral with the pane 11 on each end thereof and projecting over notched areas 21 and 22 fit in corresponding shallow recesses such as 61 illustrated in FIG. 8, in the frame, at opposite ends of the slot 23, to help retain the pane in position.

Figure 6A:
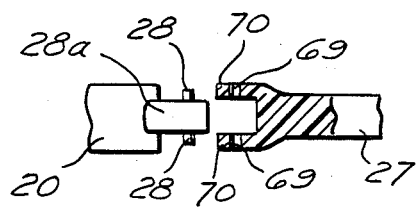
FIG. 6a is an inner side view of the ear stem detached from the top frame.
Figure 6:
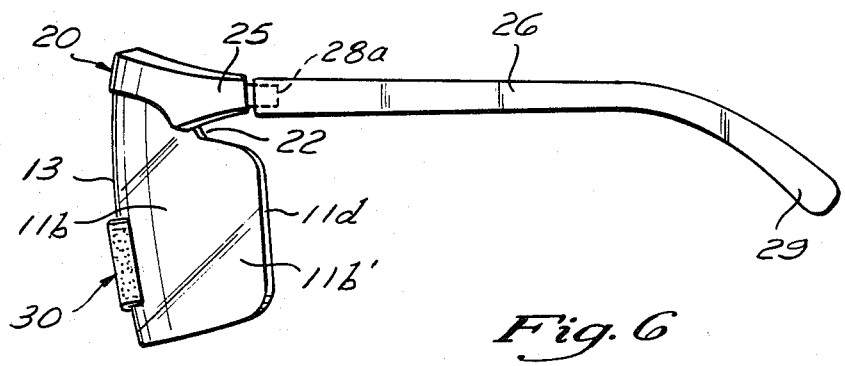
FIG. 6 is a side view of the assembled sunglasses on lines 6—6 of FIG. 2.

The top frame has enlarged end terminals at 24 and 25, portions of which extend in notched areas 21 and 22. In addition, terminals 24 and 25 are movably attached to two stems or arms 26 and 27 adapted to extend rearwardly to the wearer's ears. See FIGS. 6 and 7. Attachment may be, for example, by trunnions 28 or tongues 28a integral with top frame 20, and the bearings or openings 69 in flanges 70 integral with the stem, illustrated in FIG. 6a. These elements may be of molded, resilient plastic construction and designed to forcibly interfit, and to allow forcible "pull-away" as during impact, for the safety of the wearer. Stems 26 and 27 hook at 29 over the wearer's ears, and may also consist of molded plastic material.

A nose piece 30 may be provided as illustrated in FIGS. 6 and 10–12, which bounds the pane upwardly humped lower edge 31 (FIG. 1). The nose piece is provided with terminals 32 and 33 which are laterally spaced apart to be located along the edge 31 of the pane. The nose piece has upwardly extending sections 30a which taper toward one another, in matched relation to the pane edge 31. An upwardly convex section 30b interconnects the sections 30a. The nose piece has a slot formed therein to extend along upside down V or wave-shaped length of the nose piece for removable interfit with the upwardly humped lower edge 31 of pane 11.

FIGS. 20 and 21 show the nose piece 30 as channel-shaped in cross section, with flanges 30a that taper towards one another, to be spread apart upon reception of the pane, as seen in FIG. 20, providing a removable grip or retention of these elements.

The nose piece 30 preferably comprises a relatively soft elastomeric material having a coefficient of sliding friction that increases when the material is wet. Such a material is preferably hydrophilic and tends to retain the nose piece in position on the wearer's upper nose area as the wearer perspires, or encounters moisture as during skiing. Also, the preferred material is soft, for comfort. One such material is KROTON G, a product of Shell Oil Company.

FIGS. 10–12 show the provision of elastomeric pads 70 connected to the nose piece 30, and adapted to flex and closely fit the opposite sides of the wearer's nose. A V-shaped elastomeric connector 71 joins the pads to reinforce them and yieldably resist pad flexing. Connector 71 parallels the curvature of the nose piece at 30b, , and they define a ventilation slot 73 therebetween to pass air to the rear side of the pane 11 bridge section 13, to resist fogging.

The nose piece 30 and attached pads 70 may be removed relatively downwardly, and replaced with a selected substitute having different size, shape or color to meet the needs of the wearer. The top frame may also be easily removed upwardly from the pane and replaced with a different size or color frame. Alternatively, the pane itself may be replaced with a substitute having different sun blocking shading or composition, color, etc. Thus, the wearer or user may assemble his sunglasses from a large number of different components, as provided on a rack or other display, to result in an assembled sunglasses truly best fitted and best suited, component-wise, in every respect to the requirements of the wearer.

The notches or notched areas 21 and 22 that extend downwardly proximate the attachments of the hinged connections of the arms to the top frame also open sidewardly due to the curvature of the lens. It is found such upper notches draw discharge moisture collecting on the rearward surfaces of the pane and below the top frame (which projects rearwardly from the top of the pane). Such discharge is believed due to an aspirating affect of air directed laterally toward the notches at the front of the pane during forward movement of the wearer (as for example, a skier). Also, air turbulence at the rear side of the pane is reduced due to presence of the notches. Accordingly, the wearer's eyes are further protected from air turbulence and moisture, and during skiing, wind surfing, etc.

The frame 20 may also be provided with a second slot 80 sunk in its rearward side (see FIG. 9) to receive a tongue portion 81a of a foam pad strip 81. Padding 81 is adapted to engage the wearer's forehead, for comfort, whereby the sunglasses are yieldably supported on the wearer's nose by flexing elastomeric pads 70, and by engagement of pad 80 with the wearer's forehead, as during force application to the sunglasses toward the wearer's face.

FIG. 18 shows the nose portion 170 of a modified lens sheet 171 which is otherwise constructed as is lens sheet 11. It has an inverted V-shaped lower edge and upwardly facing shoulders 172 that act to block downward displacement of the lower ends 32 and 33 of the V-shaped nose piece 30, seen in FIG. 10. The lens sheet has two pairs of edges, each shoulder 172 extending between the edges 174 and 175 of each pair. As the nose piece 30 is pushed upwardly into position, its leg sections 30a ultimately snap outwardly away from one another so that the lowermost end of each leg section engages a shoulder 172. Note that each leg section is grooved, as at 30d, , to receive the edge extent of the lens sheet. To remove the nose piece, the leg sections are press-deflected toward one another so that the lower ends of the leg sections clear the shoulders 172, and the nose piece is then removed downwardly.

Although this invention has been described in terms of certain preferred embodiments, other embodiments that are apparent to those of ordinary skill in the art are also within the scope of this invention. Accordingly, the scope of this invention is intended to be limited only by the appended claims.

What is claimed is:

1. A lens for eyeglasses, said lens adapted for mounting on a wearer by means of an eyeglass frame having a lens receiving portion and a pair of ear stems, said lens being suitable for participation in active sports, such as biking, skiing and the like, said lens comprising:
- a unitary pane having an upper edge and a lower edge, said lower edge having a nose piece opening formed therein for mounting said lens on the nose of the wearer, thereby mounting said lens in cooperation with the eyeglass frame on the head on the wearer, said upper edge of said lens having a generally upwardly arcuate configuration to maximize the surface area of said lens above the eye level of said wearer in order to intercept light rays incident from above,
- said nose piece opening having an upper extremity, the distance separating the upper extremity of the nose piece and the upper edge of the pane being defined as $d_1$, and the distance separating the upper edge of the pane and the lower edge of the pane being defined as $d_2$, wherein $d_1$ is in the range between about $\frac{3}{4}$-inch and $1\frac{1}{2}$ inches, and $d_2$ is in the range from about $1\frac{3}{4}$ inches to $2\frac{3}{4}$ inches, said dimensions providing optimum interception of light rays while allowing sufficient ventilation around the face of the wearer while participating in active sports,
- said lens having a first arcuate cross-sectional configuration in a horizontal direction from a first ear stem to a second ear stem, having a radius designated $R_1$, wherein the arc length (L) of said lens is in the range of about $5\frac{1}{2}$ inches to about 7 inches,
- said lens having a second arcuate cross-sectional configuration in a vertical direction, having a radius designated $R_2$; and
- means for mounting said lens on said lens-receiving portion of said frame, wherein $R_1 < R_2$, and $R_1$ is in the range of about 2 inches to about 4 inches.

2. The lens of claim 1, wherein the ratio of $d_2$ to L is in the range of about 0.30 to about 3.50.

3. The lens of claim 1, wherein $R_1$ is in the range of from about 2.75 inches to about 3.50 inches.

4. The lens of claim 1, wherein $R_2 \geq 1.10 \, R_1$.

5. The lens of claim 1, wherein said horizontal arc length L comprises a central region which is substantially symmetrically located with respect to said nose piece and a pair of distal regions adjacent either side of said central region, said thickness of said lens being in at least one point in said central region greater than the thickness of said lens at any point within at least one of said distal regions.

6. The lens of claim 5, wherein said central region is symmetrically located with respect to the midpoint along said arc length L, and wherein the thickness of said lens at said midpoint is between about 0.050 and about 0.090 inch.

7. The lens of claim 6, wherein the thickness of said lens at a point approximately 45° along said arc length L from said midpoint is from about 40% to about 99% of the thickness of said lens at said midpoint.

8. The lens of claim 6, wherein the thickness of said lens at a point about 45° along said arc length of said lens from said midpoint is about 75% to about 98% of the thickness of said lens at said midpoint.

9. The lens of claim 5, wherein the thickness of said lens at said midpoint is between about 0.060 to about 0.070 inch, and the thickness of said lens in each of said distal regions is between about 0.040 and about 0.050 inch.

10. A lens for eyeglasses for participation in active sports, such as biking, skiing and the like, said lens comprising:
- a single pane, unitary lens having an upper edge and a lower edge, said lower edge having a nose piece opening formed therein for mounting said lens on the nose of the wearer,
- said nose piece opening having an upper extremity, the distance separating the nose piece upper extremity and the upper edge of the lens being defined as $d_1$, and the distance separating the upper edge of the lens and the lower edge of the lens being defined as $d_2$, wherein $d_1$ is in the range of about $\frac{3}{4}$-inch to $1\frac{1}{2}$ inches, and $d_2$ is in the range of about $1\frac{3}{4}$ inches to $2\frac{3}{4}$ inches, said dimensions providing optimum interception of light rays while allowing sufficient ventilation around the face of the wearer while participating in active sports,
- said lens having an arcuate horizontal cross-sectional configuration wherein the arc length (L) of said lens is in the range of from about $5\frac{1}{2}$ inches to 7 inches, and wherein the radius of said arc is defined by $R_1$,
- said lens having an arcuate vertical cross-sectional configuration having a radius defined by $R_2$, wherein $R_1 < R_2$ and $R_1$ is within the range of about 3 inches to 4 inches.

11. A lens for eyeglasses, said lens being suitable for participation in active sports, such as biking, skiing and the like, said lens comprising:
- a single pane, unitary lens having an upper edge and a lower edge, said lower edge having a nose piece opening formed therein for mounting said lens on the nose of the wearer,
- said lens having an arcuate cross-sectional configuration along a horizontal plane with a radius $R_1$,
- said lens having an arcuate cross-sectional configuration along a vertical plane with a radius $R_2$, wherein $R_1$ is in the range of about 2 inches to about 4 inches, and $R_2 \geq 1.10 \, R_1$.

12. The lens of claim 11, wherein said arcuate cross-sectional configuration of said lens along said horizontal plane is comprised of a central region and a pair of adjacent, distal regions, the thickness of said lens in said distal regions being less than the average thickness of said lens in said central region.

13. The lens of claim 12, wherein the thickness of said lens at the midpoint of said central region tapers substantially evenly to a reduced thickness in said distal regions.

* * * * *